(12) United States Patent
Genta et al.

(10) Patent No.: US 10,792,588 B2
(45) Date of Patent: Oct. 6, 2020

(54) ORGANIC MATERIAL PRODUCTION SYSTEM USING BIOMASS MATERIAL AND METHOD

(75) Inventors: Minoru Genta, Hyogo (JP); Ryosuke Uehara, Hyogo (JP); Kinya Fujita, Hyogo (JP); Tsuyoshi Sakaki, Saga (JP); Noriyuki Yamada, Saga (JP); Katsuichi Saito, Hokkaido (JP); Naoto Hashimoto, Hokkaido (JP); Yasuhiro Hasa, Hokkaido (JP)

(73) Assignees: MITSUBISHI HITACHI POWER SYSTEMS ENVIRONMENTAL SOLUTIONS, LTD., Yokohama-shi, Kanagawa (JP); NATIONAL INSTITUTE OF ADVANCED SCIENCE AND TECHNOLOGY, Tokyo (JP); INCORPORATED ADMINISTRATIVE AGENCY NATIONAL AGRICULTURE AND FOOD RESEARCH ORGANIZATION, Tsukuba-shi, Ibaraki (JP)

( * ) Notice: Subject to any disclaimer, the term of this patent is extended or adjusted under 35 U.S.C. 154(b) by 0 days.

(21) Appl. No.: 12/865,273

(22) PCT Filed: Sep. 19, 2008

(86) PCT No.: PCT/JP2008/067039
§ 371 (c)(1),
(2), (4) Date: Jul. 29, 2010

(87) PCT Pub. No.: WO2009/096061
PCT Pub. Date: Aug. 6, 2009

(65) Prior Publication Data
US 2011/0003348 A1 Jan. 6, 2011

(30) Foreign Application Priority Data
Feb. 1, 2008 (JP) ................. 2008-023185

(51) Int. Cl.
| | | |
|---|---|---|
| *B01D 11/02* | (2006.01) | |
| *C08H 8/00* | (2010.01) | |
| *C08B 37/00* | (2006.01) | |
| *B09B 3/00* | (2006.01) | |
| *C12P 7/10* | (2006.01) | |
| *C12M 1/00* | (2006.01) | |

(52) U.S. Cl.
CPC ............ *B01D 11/0223* (2013.01); *B09B 3/00* (2013.01); *C08B 37/0006* (2013.01); *C08H 8/00* (2013.01); *C12M 21/12* (2013.01); *C12M 43/02* (2013.01); *C12M 45/09* (2013.01); *C12M 45/20* (2013.01); *C12P 7/10* (2013.01); *Y02E 50/16* (2013.01); *Y02E 50/17* (2013.01)

(58) Field of Classification Search
CPC ........ C12P 7/10; C12P 2201/00; C07C 29/86; Y02E 50/16; A23K 1/007; C10G 2300/1011; C10G 2300/4006; C10G 65/12; C12M 43/02; C12M 47/10; C13K 1/02; C10L 2290/06; B01D 2011/002; B09B 3/0083; C02F 1/025; C02F 11/10; C02F 2209/02
USPC ...................................................... 435/289.1
See application file for complete search history.

(56) References Cited

U.S. PATENT DOCUMENTS

| | | |
|---|---|---|
| 3,833,461 A | 9/1974 | Woodruff |
| 3,985,725 A | 10/1976 | Lin |
| 3,985,728 A | 10/1976 | Lin |
| 4,023,982 A | 5/1977 | Knauth |
| 4,152,197 A | 5/1979 | Lindahl et al. |
| 4,443,540 A | 4/1984 | Chervan et al. |
| 4,650,689 A | 3/1987 | Hedrick |

(Continued)

FOREIGN PATENT DOCUMENTS

| | | |
|---|---|---|
| BR | 0613681-8 A2 | 7/2010 |
| BR | 1009205-6 A2 | 4/2016 |

(Continued)

OTHER PUBLICATIONS

Ando et al. Decomposition behavior of plant biomass in hot-compressed water. Ind Eng Chem Res. 2000;39:3688-3693.*

(Continued)

*Primary Examiner* — Lynn Y Fan
(74) *Attorney, Agent, or Firm* — Westerman, Hattori, Daniels & Adrian, LLP

(57) ABSTRACT

An organic material production system includes: a pretreatment device (12) that pulverizes a biomass material (11); a hydrothermal decomposition apparatus (14) that hydrothermally decomposes a pulverized biomass (13) by causing it to countercurrently contact with hot compressed water (15), elutes lignin components and hemicellulose components into the hot compressed water (15), and separates the lignin components and the hemicellulose components from a biomass solid residue; a first enzymatic hydrolysis device (19-1) that treats cellulose in a biomass solid residue (17), discharged from the hydrothermal decomposition apparatus, with an enzyme (18) to enzymatically hydrolyze it to a sugar solution containing hexose; a fermenter (21) that produces ethanol by fermentation using a sugar solution (20) obtained by the first enzymatic hydrolysis device (19-1); and a refiner 25 that refines an alcohol fermentation liquid (22), so as to separate it into ethanol (23) and a residue (24).

2 Claims, 2 Drawing Sheets

(56) References Cited

U.S. PATENT DOCUMENTS

| | | |
|---|---|---|
| 4,746,401 A | 5/1988 | Roberts et al. |
| 4,859,322 A | 8/1989 | Huber |
| 5,348,871 A | 9/1994 | Scott et al. |
| 5,411,594 A | 5/1995 | Brelsford |
| 5,424,417 A | 6/1995 | Torget et al. |
| 5,466,108 A | 11/1995 | Piroska |
| 5,846,787 A | 12/1998 | Ladisch et al. |
| 6,022,419 A | 2/2000 | Torget et al. |
| 6,039,774 A | 3/2000 | McMullen et al. |
| 6,419,788 B1 | 7/2002 | Wingerson |
| 8,123,864 B2 | 2/2012 | Christensen et al. |
| 8,163,517 B2 | 4/2012 | Genta et al. |
| 8,497,091 B2 | 7/2013 | Hanakawa et al. |
| 8,728,770 B2 | 5/2014 | Ishikawa et al. |
| 8,765,405 B2 | 7/2014 | Kurihara et al. |
| 9,102,956 B2 | 8/2015 | Genta et al. |
| 9,157,107 B2 | 10/2015 | Hanakawa et al. |
| 10,093,747 B2 | 10/2018 | Kurihara et al. |
| 2002/0151034 A1 | 10/2002 | Zhang et al. |
| 2006/0280663 A1 | 12/2006 | Osato et al. |
| 2007/0231869 A1 | 10/2007 | Holmgren et al. |
| 2007/0259412 A1 | 11/2007 | Belanger et al. |
| 2008/0026431 A1 | 1/2008 | Saito et al. |
| 2008/0028675 A1 | 2/2008 | Clifford, III et al. |
| 2008/0032344 A1 | 2/2008 | Fallavollita |
| 2008/0044891 A1 | 2/2008 | Kinley et al. |
| 2008/0299628 A1 | 12/2008 | Hallberg et al. |
| 2008/0299630 A1 | 12/2008 | Mclennan et al. |
| 2009/0077729 A1 | 3/2009 | McLeod |
| 2009/0283397 A1 | 11/2009 | Kato et al. |
| 2009/0311752 A1 | 12/2009 | Bodie et al. |
| 2010/0108567 A1 | 5/2010 | Medoff |
| 2010/0184176 A1 | 7/2010 | Ishida et al. |
| 2010/0269990 A1 | 10/2010 | Dottori et al. |
| 2010/0285574 A1* | 11/2010 | Genta et al. ............... 435/289.1 |
| 2010/0317843 A1 | 12/2010 | Sudhakaran et al. |
| 2010/0330638 A1 | 12/2010 | Aita et al. |
| 2011/0079219 A1 | 4/2011 | McDonald et al. |
| 2011/0250637 A1 | 10/2011 | Kurihara et al. |
| 2011/0314726 A1 | 12/2011 | Jameel et al. |
| 2012/0006320 A1 | 1/2012 | Nguyen |
| 2012/0009626 A1 | 1/2012 | Suzuki et al. |
| 2012/0009642 A1 | 1/2012 | Suzuki et al. |
| 2012/0315683 A1 | 12/2012 | Mosier et al. |
| 2014/0004571 A1 | 1/2014 | Garrett et al. |
| 2014/0273127 A1 | 9/2014 | Fuchs et al. |
| 2014/0287461 A1 | 9/2014 | Kurihara et al. |

FOREIGN PATENT DOCUMENTS

| | | |
|---|---|---|
| CA | 2 448 862 A1 | 9/2002 |
| CA | 2 660 990 A1 | 8/2009 |
| CA | 2654306 A1 | 8/2009 |
| CA | 2666152 A1 | 4/2010 |
| CA | 2 750 754 A1 | 1/2012 |
| CA | 2654306 C | 10/2013 |
| EP | 0 098 490 A2 | 1/1984 |
| JP | 9-507386 A | 7/1997 |
| JP | 11-172262 A | 6/1999 |
| JP | 11-506934 A | 6/1999 |
| JP | 3042076 B2 | 5/2000 |
| JP | 2001-170601 A | 6/2001 |
| JP | 2002-059118 A | 2/2002 |
| JP | 2002-105466 A | 4/2002 |
| JP | 2003-219900 A | 8/2003 |
| JP | 2003-311141 A | 11/2003 |
| JP | 2004-105855 A | 4/2004 |
| JP | 2005-027541 A | 2/2005 |
| JP | 2005-168335 A | 6/2005 |
| JP | 2005-205252 A | 8/2005 |
| JP | 2005-229821 A | 9/2005 |
| JP | 2005-534343 A | 11/2005 |
| JP | 2006-036977 A | 2/2006 |
| JP | 2006-136263 A | 6/2006 |
| JP | 2006-223152 A | 8/2006 |
| JP | 2006-289164 A | 10/2006 |
| JP | 2007-112880 A | 5/2007 |
| JP | 2007-202560 A | 8/2007 |
| JP | 2007-301472 A | 11/2007 |
| JP | 2008-054608 A | 3/2008 |
| JP | 2008-104452 A | 5/2008 |
| JP | 2008-278825 A | 11/2008 |
| JP | 2009-183153 A | 8/2009 |
| JP | 2009-183154 A | 8/2009 |
| JP | 2009-183805 A | 8/2009 |
| JP | 2010-17084 A | 1/2010 |
| JP | 4764527 B1 | 9/2011 |
| JP | 4764528 B1 | 9/2011 |
| PL | 0613681-8 A2 | 7/2010 |
| PL | 1009205-6 A2 | 4/2016 |
| WO | 84/003304 A1 | 8/1984 |
| WO | 1995/017517 A1 | 6/1995 |
| WO | 96/18590 A1 | 6/1996 |
| WO | 1996/040970 A1 | 12/1996 |
| WO | 2004/037973 A2 | 5/2004 |
| WO | 2007/009463 A2 | 1/2007 |
| WO | 2008017145 A1 | 2/2008 |
| WO | 2009/096060 A1 | 8/2009 |
| WO | 2009/096061 A1 | 8/2009 |
| WO | 2009-096062 A1 | 8/2009 |
| WO | 2009/110374 A1 | 9/2009 |
| WO | 2009/124240 A1 | 10/2009 |
| WO | 2010/038302 A1 | 4/2010 |
| WO | 2010067785 A1 | 5/2012 |
| WO | 2013/082616 A2 | 6/2013 |

OTHER PUBLICATIONS

Olsson et al. Fermentation of lignocellulosic hydrolysates for ethanol production. Enzyme and Microbial Technology. 1996;18:312-331.*

Garrote et al. Hydrothermal processing of lignocellulosic materials. Holz als Roh- und Werkstoff. 1999;57:191-202.*

Mosier et al. Features of promising technologies for pretreatment of lignocellulosic biomass. Bioresource Technology. 2005.96:673-686.*

Nilsson A. Control of fermentation of lignocellulosic hydrolysates. Department of Chemical Engineering II, Lund University, Sweden. 1999;1-6.*

Liu et al. Continuous fermentation of hemicellulose sugars and cellulose to ethanol. International Symposia on Alcohol Fuels. 2005;1-28.*

Lehrburger E. Developing biorefineries to produce energy, ethanol and other industrial products. PureVision Technology, Inc. Alternative Energy Conference;1-26.*

Carrasco et al. Effects of dilute acid and steam explosion pretreatments on the cellulose structure and kinetics of cellulosic fraction hydrolysis by dilute acids in lignocellulosic materials. Applied Biochemistry and Biotechnology. 1994;45/46;23-34.*

Kohlmann et al. Enhanced enzyme activities on hydrated lignpcellulosic substrates. In: Saddler, J.N., Penner, M.H. (Eds.), Enzymatic Degradation of Insoluble Carbohydrates. Acs Publishing. 1995.237-255.*

Zufle et al. Catalytic combustion in a reactor with periodic flow reversal. Part 2. Steady-state reactor model. Chemical Engineering and Processing. 1997;36:341-352.*

"Biomass Ethanol", Nikkei Biotechnology & Business, Sep. 2002, pp. 52-61, partial translation.

"Biomass—Extensive Use of Bioresources", Japanese Society for Bioscience, Biotechnology, and Agrochemistry, Sep. 1985, pp. 90-93, partial translation.

International Search Report of PCT/JP2008/067039, dated Dec. 16, 2008.

Japanese Office Action dated Dec. 15, 2009, issued in corresponding Japanese Patent Application No. 2008-023185.

Japanese Office Action dated Oct. 23, 2012, issued in corresponding Japanese Patent Application No. 2009-245963, with English translation (5 pages).

(56) References Cited

OTHER PUBLICATIONS

Canadian Notice of Allowance dated Aug. 22, 2013, issued in corresponding Canadian Patent Application No. 2,713,529.
Indonesian Notice of Allowance dated Jun. 26, 2013, issued in corresponding Indonesian Patent Application No. W-00200902415, w/English translation.
Arroyo-Lopez, F.N. et al., "Effects of temperature, pH and sugar concentration on the growth parameters of Saccharomyces cerevisiae, S. kudriavzevii and their interspecific hybrid", International Journal of Food Microbiology, vol. 131, pp. 120-127 (2009).
Turton, L.J. et al., "Effect of Glucose Concentration in the Growth Medium Upon Neutral and Acidic Fermentation End-products of Clostridium Bifermentans, Clostridium Sporogenes and Peptostreptococcus Anaerobius", J. Med. Microbiol., vol. 16, pp. 61-67 (1983).
Dien, B.S. et al., "Fermentation of hexose and pentose sugars using a novel ethanologenic Escherichia coli strain", Enzyme and Microbial Technology, vol. 23, pp. 366-371 (1998).
U.S. Office Action dated Aug. 19, 2013 issued in U.S. Appl. No. 13/578,116.
U.S. Office Action dated Oct. 3, 2013 issued in U.S. Appl. No. 13/782,545.
Canadian Notice of Allowance dated Aug. 22, 2013, issued in Canadian Patent Application No. 2666152.
Canadian Notice of Allowance dated Aug. 22, 2013, issued in Canadian Patent Application No. 2713529.
U.S. Office Action dated Oct. 28, 2013, issued in U.S. Appl. No. 12/443,515.
U.S. Office Action dated Oct. 7, 2013, issued in U.S. Appl. No. 13/700,753.
U.S. Restriction/Election dated Aug. 22, 2013, issued in U.S. Appl. No. 13/700,753.
U.S. Final Office Action dated Jul. 3, 2014, issued in U.S. Appl. No. 13/578,116 (17 pages).
U.S. Final Office Action dated Aug. 18, 2014, issued in U.S. Appl. No. 13/132,034 (30 pages).
U.S. Final Office Action dated Jun. 13, 2014, issued in U.S. Appl. No. 12/438,792 (26 pages).
U.S. Non-Final Office Action dated Aug. 27, 2014, issued in U.S. Appl. No. 13/132,040 (53 pages).
U.S. Final Office Action dated Jul. 22, 2014, issued in U.S. Appl. No. 12/443,515 (13 pages).
Kumagai Satoshi et al. "Fractionation and Saccharification of Cellulose and Hemicellulose in Rice Hull by Hot-Compressed-Water Treatment with Two-Step Heating", Journal of the Japan Institute of Energy, Dec. 1, 2003 vol. 83, pp. 776-781, Cited in Notice of Acceptance dated Mar. 4, 2014, issued in Japanese Patent Application No. 2009-252201.
U.S. Non-Final Office Action dated Mar. 10, 2014, in U.S. Appl. No. 13/782,545 (27 pages).
Decision of a Patent Grant dated Mar. 4, 2014, issued in JP2009-252201 (corresponding to U.S. Appl. 12/443,515), w/English translation (4 pages).
Decision of a Patent Grant dated Mar. 4, 2014, issued in JP2009-245963 (corresponding to U.S. Appl. No. 12/438,792) w/English translation (4 pages).
Australian Notice of Acceptance dated Mar. 17, 2014, issued in Australian patent application No. 2011355013 (corresponding to U.S. Appl. No. 13/578,116) (2 pages).
U.S. Office Action dated Apr. 14, 2014, issued in U.S. Appl. No. 12/443,515 (16 pages).
U.S. Non-Final Office Action dated Dec. 17, 2013, issued in related U.S. Appl. No. 13/203,929 (23 pages).
U.S. Non-Final Office Action dated Dec. 16, 2013, issued in related U.S. Appl. No. 13/132,034 (29 pages).
Gregg, D. et al., "Bioconversion of Lignocellulosic Residue to Ethanol: Process Flowsheet Development", Biomass and Bioenergy, 1995, vol. 9, No. 1-5, pp. 287-302, Cited in U.S. Office Action dated Dec. 17, 2013.
Canadian Office Action dated Nov. 8, 2013, issued in Canadian Patent Application No. 2,801,383 (2 pages).

Indonesian Notice of Allowance dated Nov. 15, 2013, issued in Indonesian Patent Application No. W-00201002623, w/English translation, (5 pages).
U.S. Non-Final Office Action dated Jan. 30, 2014 issued in related U.S. Appl. No. 12/438,792 (39 pages).
Canadian Notice of Allowance dated Jan. 13, 2014, issued in Canadian Patent Application No. 2,744,522 (1 page).
U.S. Non-Final Office Action dated Jan. 30, 2014, issued in related U.S. Appl. No. 13/578,116 (22 pages).
Genta, "NEDO ni yoru Biomass Energy to Ko Koritsu Tenkan Gijutsu Kaihatsu 1), Suinetsu Bunkaiho to Koso Bunkaiho wo Kumiawaseta Nogyo Zansa to no Celluose-kei Biomass no Tei Cost Toka Gijutsu no Kaihatsu" Clean Energy, 2010, pp. 11-15, cited in the Australian Notice of Acceptance dated Mar. 17, 2014, which was previously submitted in the IDS on Apr. 30, 2014.
Canadian Office Action dated Mar. 31, 2014, issued in Canadian Patent Application No. 2,750,753 (3 pages) (corresponding to U.S. Appl. No. 13/203,929).
U.S. Final Office Action dated May 22, 2014 issued in U.S. Appl. No. 13/700,753 (40 pages).
U.S. Final Office Action dated Jun. 3, 2014, issued in U.S. Appl. No. 13/203,929 (22 pages).
Genda, M. et al., "Suinetsu Bunkaiho to Koso Bunkaiho o Kumiawaseta Nogyo Zansa To no Cellulose Biomass no Tei Cost Toka Gijutsu no Kaihatsu", Heisei 21 Nendo Biomass Energy Kanren Jigyo Seika Hokokukai, Feb. 11, 2010, pp. 55-69, URL: http://www.nedo.go.jp/events/report/FF_00003.html, Cited in JP Office Action dated Oct. 14, 2014.
U.S. Office Action dated Sep. 30, 2014, issued in U.S. Appl. No. 13/782,545 (43 pages).
Japanese Office Action dated Oct. 14, 2014, issued in Japanese Patent Application No. 2010-154233 (corresponds to U.S. Appl. No. 13/700,753), with English Translation (7 pages).
U.S. Office Action dated Dec. 5, 2014, issued in U.S. Appl. No. 13/121,969.
Canadian Notice of Allowance dated Dec. 5, 2014, issued in Canadian Patent Application No. 2750754 (corresponds to U.S. Appl. No. 13/203,848).
Indonesian Office Action dated Oct. 29, 2014, issued in Indonesian Patent Application No. W00201103522 (corresponds to U.S. Appl. No. 13/203,929), w/English translation.
U.S. Notice of Allowance dated Nov. 5, 2014, issued in U.S. Appl. No. 12/443,515.
U.S. Office Action dated Dec. 26, 2014, issued in U.S. Appl. No. 13/132,040.
Indonesian Office Action dated Nov. 14, 2014, issued in IDW-00201102352, w/English translation (corresponds to U.S. Appl. No. 131121,969) (7 pages).
Indoniesian Office Action dated Nov. 7, 2014, issued in IDW-00200902414, w/English translation (corresponds to U.S. Appl. No. 12/438,792) (6 pages).
Non-Final Office Action dated Jun. 19, 2015, issued in U.S. Appl. No. 13/700,753 (34 pages).
International Search Report dated Jul. 3, 2012 issued in International Application No. PCT/JP2012/058460 (corresponds to U.S. Appl. No. 14/381,511).
Written Opinion of the International Searching Authority dated Jul. 3, 2012 issued in International Application No. PCT/JP2012/058460 (corresponds to U.S. Appl. No. 14/381,511).
Decision of a Patent Grant dated Nov. 12, 2013, issued in Japanese Patent Application No. 2013-536355, w/English translation (corresponds to U.S. Appl. No. 14/381,511) (4 pages).
U.S. Office Action dated Apr. 24, 2015, issued in U.S. Appl. No. 14/381,511 (20 pages).
Notice of Allowance and Fee(s) Due dated Feb. 17, 2015, issued in U.S. Appl. No. 13/782,545 (20 pages).
U.S. Office Action dated Mar. 19, 2015, issued in U.S. Appl. No. 13/121,969 (21 pages).
U.S. Office Action dated Mar. 13, 2015, issued in U.S. Appl. No. 13/722,385 (41 pages).
Notice of Allowance and Fee(s) Due dated Apr. 2, 2015, issued in U.S. Appl. No. 13/132,040 (17 pages).

(56) References Cited

OTHER PUBLICATIONS

U.S. Office Action dated May 13, 2015, issued in U.S. Appl. No. 12/438,792 (11 pages).
Final Office Action dated Aug. 6, 2015, issued in U.S. Appl. No. 14/381,511 (14 pages).
Notice of Allowance dated Aug. 19, 2015, issued in U.S. Appl. No. 12/438,792 (12 pages).
Notice of Allowance dated Aug. 12, 2015, issued in U.S. Appl. No. 13/578,116 (48 pages).
Non-Final Office Action dated Aug. 21, 2015, issued in U.S. Appl. No. 13/203,929 (18 pages).
Notice of Allowance dated Jul. 6, 2015, issued in Indonesian application No. W-00201103522 (counterpart of U.S. Appl. No.13/203,929) with English translation (4 pages).
Decision of a patent grant dated Nov. 10, 2015 issued in counterpart Japanese patent application No. 2010-154233, with English translation, (5 pages).
Final Office Action dated Sep. 28, 2015, issued in U.S. Appl. No. 13/203,848 (34 pages).
Office Action dated Jul. 10, 2015, issued in counterpart Australian Patent Application No. 2012374915 (5 pages).
Notice of Allowance dated Sep. 30, 2015, issued in counterpart Canadian Patent Application No. 2,791,665 (1 page).
Final Office Action dated Sep. 28, 2015, issued in U.S. Appl. No. 13/722,385 (20 pages).
Decision of patent grant dated Nov. 10, 2015 issued in Japanese patent Application No. 2010-154233, with English translation (5 pages) counterpart of U.S. Appl. No. 13/700,753.
Office Action dated Jul. 10, 2015, issued in Australian Patent Application No. 2012374915 (5 pages), counterpart of U.S. Appl. No. 14/381,511.
Notice of Allowance dated Sep. 30, 2015, issued in Canadian Patent Application No. 2,791,665 (1 page), counterpart of U.S. Appl. No. 13/578,116.
Notice of Allowance dated Dec. 21, 2015, issued in U.S. Appl. No. 14/381,511 (11 pages).
Supplemental Notice of Allowability dated Jan. 8, 2016, issued in U.S. Appl. No. 14/381,511 (6 pages).
Notice of Allowance dated Feb. 3, 2016, issued in U.S. Appl. No. 13/578,116 (17 pages).
Notice of Allowance dated May 5, 2016, issued in U.S. Appl. No. 13/203,848.
Notice of Allowance dated Mar. 30, 2016, issued in Indonesian Patent Application No. W-00200902414, with English translation, counterpart of U.S. Appl. No. 12/430,792. (4 pages).
Notice of Acceptance dated Mar. 16, 2016, issued in Australian Application No. 2012374915, counterpart of U.S. Appl. No. 14/381,511 (2 pages).
Final Office Action dated Apr. 22, 2016, issued in U.S. Appl. No. 13/132,034.
Notice of Allowance dated Mar. 14, 2016, issued in U.S. Appl. No. 13/121,969. (12 pages).
Non-final Office Action dated Apr. 18, 2016, issued in U.S. Appl. No. 13/722,385.
Non-Final Office action dated Sep. 25, 2015, issued in U.S. Appl. No. 13/132,034 (39 pages).
Notification of Allowance dated Aug. 8, 2016, issued in Indonesian Patent Application No. W-00201102351, with English translation. (4 pages).
Non-Final Office Action dated Oct. 7, 2016, issued in U.S. Appl. No. 13/132,034. (27 pages).
Notice of Allowance dated Oct. 5, 2016, issued in U.S. Appl. No. 13/722,385. (33 pages).
Office Action dated Sep. 29, 2016, issued in co-pending U.S. Appl. No. 14/411,473 (English; 33 pages; w/ PTO-892 and returned PTO/SB/08 forms).
Notification of Result of Substantive Examination dated Mar. 30, 2016, issued in Indonesian Patent Application No. W-00201102351, with English translation. (4 pages).
Final Office Action dated May 26, 2017, issued in U.S. Appl. No. 13/132,034.
Notice of Allowance dated Sep. 8, 2017, issued in U.S. Appl. No. 13/203,929.
Final Office Action dated Sep. 21, 2017, issued in U.S. Appl. No. 13/700,753.
Notice of Allowance dated Oct. 13, 2017, issued in U.S. Appl. No. 13/132,034.
International Search Report of PCT/JP2008/067038, dated Nov. 18, 2008.
Japanese Office Action dated Oct. 23, 2012, issued in Japanese Patent Application No. 2009-252201, with English translation (9 pages).
International Search Report of PCT/JP2008/067040, dated Dec. 16, 2008.
U.S. Office Action dated Oct. 19, 2010, issued in U.S. Appl. No. 12/438,792.
U.S. Office Action dated Mar. 7, 2011, issued in U.S. Appl. No. 12/438,792.
U.S. Advisory Action dated Jun. 16, 2011, issued in U.S. Appl. No. 12/438,792.
Examiner's Answer to Appeal Brief dated Nov. 4, 2011, issued in U.S. Appl. No. 12/438,792.
U.S. Office Action dated Dec. 14, 2010, issued in U.S. Appl. No. 12/443,515.
U.S. Office Action dated Mar. 29, 2011, issued in U.S. Appl. No. 12/443,515.
Examiner's Answer to Appeal Brief dated Nov. 9, 2011, issued in U.S. Appl. No. 12/443,515.
U.S. Office Action dated Mar. 11, 2013 issued in U.S. Appl. No. 12/443,515.
Canadian Office Action dated Mar. 7, 2012, issued in Canadian Patent Application No. 2,654,306.
Canadian Office Action dated Sep. 20, 2012, issued in Canadian Patent Application No. 2,654,306.
Canadian Office Action dated Feb. 25, 2013, issued in Canadian Patent Application No. 2,654,306.
Canadian Office Action dated Feb. 16, 2012, issued in Canadian Patent Application No. 2,660,990.
Canadian Office Action dated Oct. 3, 2012, issued in Canadian Patent Application No. 2,660,990.
Canadian Office Action dated Apr. 10, 2012, issued in Canadian Patent Application No. 2,713,529.
Canadian Office Action dated Jan. 15, 2013, issued in Canadian Patent Application No. 2,713,529.
English translation of JP2007-301472 (JP reference previously submitted with IDS dated Jul. 27, 2010).
English language machine translation of WO 9618590; in U.S. Office Action dated Mar. 29, 2011.
Canadian Notice of Allowance dated Jun. 26, 2013, issued in corresponding Canadian Patent Application No. 2,654,306 (1 page).
Canadian Notice of Allowance dated Jul. 2, 2013, issued in corresponding Canadian Patent Application No. 2,660,990 (1 page).
Petersen, M. Ø. et al., "Optimization of hydrothermal pretreatment of wheat straw for production of bioethanol at low water consumption without addition of chemicals", Biomass and Biotechnology, 2009, vol. 33, pp. 834-840; cited in Brazilian Office Action dated May 8, 2018.
Silva, V.D.N., "Estudos de pré-tratamento e sacarificação enzimática de resíduos agroindustriais como etapas no processo de obenção de etanol celulósico", Dissertação de M.Sc., USP Lorena, SP, Brasil, 2009; cited in Brazilian Office Action dated May 8, 2018. (113 pages).
Technical Examination Report dated Jul. 17, 2018, issued in counterpart Brazilian Application No. 112015000255-2, with English translation (17 pages).
Technical Examination Report dated May 8, 2018, issued in counterpart Brazilian Application No. 112012030802-5, with English translation (17 pages).
Office Action, dated Jul. 5, 2019, issued in co-pending U.S. Appl. No. 13/700,753 (w/ PTO-892 form and returned PTO/SB/08a forms; 15 pages).

(56) References Cited

OTHER PUBLICATIONS

Gribovskaya, I.V. et al., "Extraction of mineral elements from inedible wastes of biological components of a life-support system and their utilization for plant nutrition", Adv. Space Res., vol. 18, No. 4/5, pp. 93-97 (1996) (in English; 5 pages; co pending U.S. Appl. No. 13/700,753).

Ibanez, E. et al., "Subcritical water extraction of antioxidant compounds from rosemary palnts", J. Agric. Food. Chem., vol. 51, No. 2, pp. 375-382 (2003) (in English; 8 pages; co-pending U.S. Appl. No. 13/700,753).

Technical Examination Report issued in counterpart BR application No. 11 2013 018992-4, with English translation. (16 pages).

Non-Final Office Action dated Jan. 11, 2019, issued in U.S. Appl. No. 13/700,753 (19 pages).

Technical Examination Report dated Dec. 3, 2019 in Brazilian patent application No. 11 2013 019285-2, which is counterpart to U.S. Appl. No. 13/982,645 that issued as U.S. Pat. No. 9,657,262 (w/ English translation; 14 pages).

* cited by examiner

ORGANIC MATERIAL PRODUCTION SYSTEM USING BIOMASS MATERIAL AND METHOD

TECHNICAL FIELD

The present invention relates to a biomass hydrothermal decomposition apparatus and a method thereof that enable efficient hydrothermal decomposition of biomass material, and to an organic material production system using biomass material, which system enables efficient production of organic materials such as alcohols, substitutes for petroleum, or amino acids by using such apparatus and method.

BACKGROUND ART

Technologies for producing ethanol or the like have been commercialized that involve converting woody biomass or other biomass into sugars with dilute sulfuric acid or concentrated sulfuric acid, and then subjecting them to solid-liquid separation, neutralizing the liquid phase thereof, and utilizing the resultant components as biomass materials for ethanol fermentation or the like (Patent Documents 1 and 2). Further, by using sugar as starting material, production of chemical industrial raw material (e.g., lactic fermentation) has been considered. Biomass as used herein refers to a living organism integrated in material circulation in the global biosphere or accumulation of organic materials derived from living organisms (see JIS K 3600 1258).

Sugarcane, corn, and other materials, currently used as alcohol raw materials, have been originally used for food. Using such food resources as long-term stable industrial resources is not preferable in view of life cycle of valuable food.

For this reason, it is a challenge to efficiently use cellulose resources such as herbaceous biomass and woody biomass, which are considered as potentially useful resources.

Cellulose resources include cellulose ranging from 38% to 50%, hemicelluloses components ranging from 23% to 32%, and lignin components, which are not used as fermentation materials, ranging from 15% to 22%. Due to many challenges, the industrial studies have been conducted targeting certain fixed materials, and no technologies have been disclosed yet on production systems taking into account diversity of the materials.

Production systems targeting fixed materials see almost no point regarding countermeasures for waste problems and global warming, because those systems have attempted such countermeasures with a method that brings more disadvantages to fermentation materials than starch materials. Thus, there has been a need for a method applicable to a variety of wastes in broader sense. Enzymatic saccharification methods are also considered as a future challenge due to its low efficiency. Acid treatment only achieves a low saccharification rate of about 75% (a basis for components that can be saccharified), due to excessive decomposition of sugar. Thus, the ethanol yield achieves only 25% by weight of cellulose resources (Non-Patent Document 1 and Patent Document 3).

[Patent Document 1] Japanese Patent Application Laid-open No. 9-507386
[Patent Document 2] Japanese Patent Application Laid-open No. 11-506934
[Patent Document 3] Japanese Patent Application Laid-open No. 2005-168335
[Non-Patent Document 1] Nikkei Biotechnology & Business, p. 52, September 2002
[Non-Patent Document 2] Biomass-Extensive Use of Bioresources, edited by Japanese Society for Bioscience, Biotechnology, and Agrochemistry, Asakura Publishing Co., Ltd., September 1985

DISCLOSURE OF INVENTION

Problem to be Solved by the Invention

In the proposals disclosed in Patent Documents 1 and 2 above, sulfuric acid necessary for reaction needs to be constantly supplied from outside the reaction system. With increasing the production scale, this poses problems, such as increasing the cost for purchasing equipment resistant to the acid and large amounts of sulfuric acid, while increasing the cost for disposing used sulfuric acid (e.g., cost for processing with a gypsum desulfulation), and the cost for recovering such sulfuric acid.

The proposal disclosed in Patent Document 3 above involves subjecting various types of cellulose resources to hydrothermal treatment, and converting them into sugars with enzymatic saccharification. During the hydrothermal treatment, cellulase inhibitors such as lignin components (Non-Patent Document 2) that inhibit enzymatic saccharification of cellulose are not removed and mixed with cellulose. This poses a problem of reducing the efficiency in cellulose enzymatic saccharification.

Other than cellulose, hemicellulose components are also contained in cellulose resources. This poses a problem that enzymes suitable for cellulose and hemicellulose components are necessary for enzymatic saccharification.

The resulting sugar solution includes a hexose solution from cellulose, and a pentose solution from hemicellulose components. For example, for alcohol fermentation, yeasts suitable for the respective solutions are necessary. Thus, alcohol fermentation needs to be improved low efficiency for fermenting a mixture of a hexose solution and a pentose solution.

As such, conventional technologies have caused a phenomenon that side reaction products inhibit enzymatic saccharification, reducing the sugar yield. Thus, what has been needed is a hydrothermal decomposition apparatus that removes inhibitors for enzymatic saccharification and thereby improves enzymatic saccharification of cellulose-based components.

In view of the foregoing problems, the present invention has an object to provide an organic material production system using biomass material, which can efficiently produce a sugar solution using such apparatus and method, and can efficiently produce various types of organic materials (e.g., alcohols, substitutes for petroleum, or amino acids) using the sugar solution as a base material.

Means for Solving Problem

To achieve the above object, according to a first invention of the present invention, an organic material production system using biomass material includes: a hydrothermal decomposition apparatus that causes the biomass material and hot compressed water to countercurrently contact with each other and undergo hydrothermal decomposition, and that transfers a lignin component and a hemicellulose component into the hot compressed water, so as to separate the lignin component and the hemicellulose component from a biomass solid residue; a first enzymatic hydrolysis device that treats, with an enzyme, cellulose in the biomass solid residue discharged from the hydrothermal decomposition apparatus, so as to enzymatically hydrolyze the cellulose to a sugar solution containing hexose; and a fermenter that produces, using the sugar solution obtained by the first enzymatic hydrolysis device, any one of alcohols, substitutes for petroleum, or amino acids by fermentation.

According to a second invention, the organic material production system according to the first invention further includes: a second enzymatic hydrolysis device that treats, with an enzyme, the hemicellulose component in discharged hot water, so as to hydrolyze the hemicellulose component to a sugar solution containing pentose; and a fermenter that produces, using the sugar solution obtained by the second enzymatic hydrolysis device, any one of alcohols, substitutes for petroleum, or amino acids by fermentation.

According to a third invention, in the organic material production system according to the first or second inventions, the hydrothermal decomposition apparatus has a reaction temperature ranging from 180° C. to 240° C.

According to a forth invention, a method for organic material production using biomass material includes: a hydrothermal decomposition process that causes the biomass material and hot compressed water to countercurrently contact with each other and undergo hydrothermal decomposition, and that transfers a lignin component and a hemicellulose component into the hot compressed water, so as to separate the lignin component and the hemicellulose component from a biomass solid residue; a first enzymatic hydrolysis process that treats, with an enzyme, cellulose in the biomass solid residue discharged from the hydrothermal decomposition apparatus, so as to enzymatically hydrolyze the cellulose to a sugar solution containing hexose; and a fermentation process that produces, using the sugar solution obtained by the first enzymatic hydrolysis process, any one of alcohols, substitutes for petroleum, or amino acids by fermentation.

According to a fifth invention, the method for organic material production according to the forth invention further includes: a second enzymatic hydrolysis process that treats, with an enzyme, the hemicellulose component in discharged hot water, so as to hydrolyze the hemicellulose component to a sugar solution containing pentose; and a fermentation process that produces, using the sugar solution obtained by the second enzymatic hydrolysis process, any one of alcohols, substitutes for petroleum, or amino acids by fermentation.

According to a sixth invention, in the method for organic material production according to the forth or fifth inventions, the hydrothermal decomposition process has a reaction temperature ranging from 180° C. to 240° C.

Effect of the Invention

According to the present invention, with use of a hydrothermal decomposition apparatus that causes counter-current contact, side reaction products (lignin components and hemicellulose components) resulting from the reaction for producing a target component, i.e., cellulose, (that is enzymatically saccharified to a hexose solution) are transferred into the hot compressed water. In this way, the cellulose-based biomass solid residue can be obtained. Accordingly, by efficiently saccharifying it to the hexose solution and using the sugar solution as a base material, various types of organic materials (e.g., alcohols, substitutes for petroleum, or amino acids) can be produced efficiently.

By causing biomass material and hot compressed water to countercurrently contact with each other, their components are sequentially discharged to the outside the reaction system in order of solubility in the hot water. Further, due to the temperature gradient from a feeding section of the biomass to a feeding section of the hot water, excessive decomposition of hemicellulose components is prevented. As a result, pentose components can be recovered efficiently.

Figure 1:
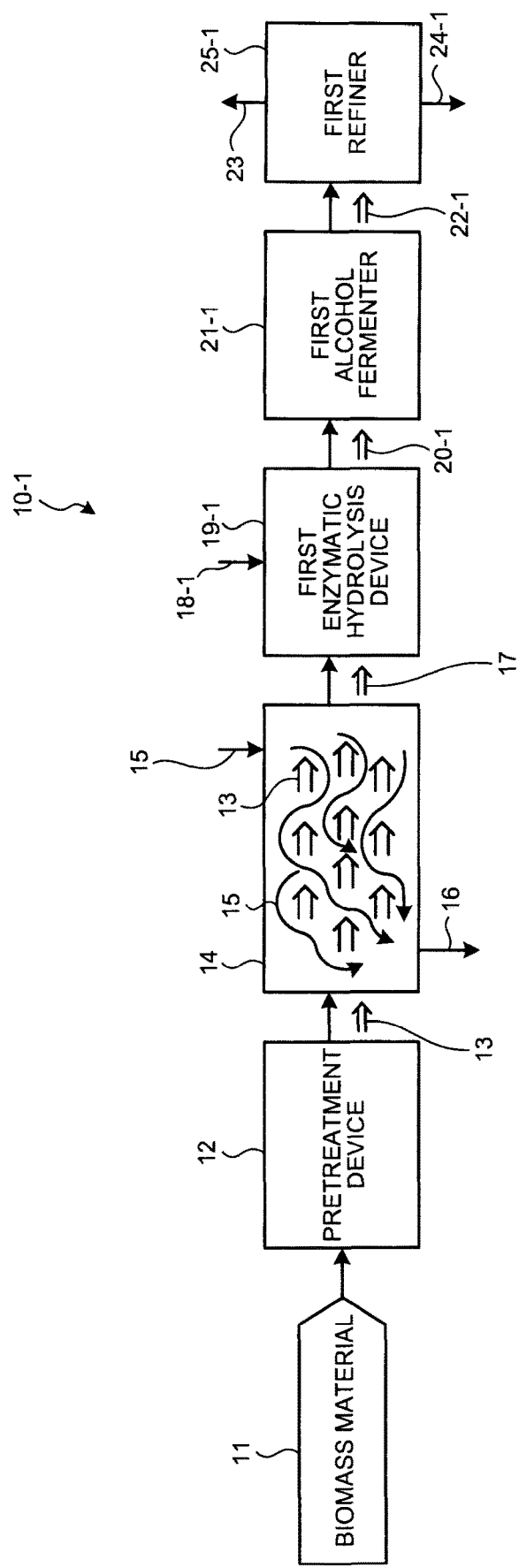
FIG. 1 is a schematic of an alcohol production system according to a first embodiment.

EXPLANATIONS OF LETTERS OR NUMERALS 11 biomass material
12 pretreatment device
13 pulverized biomass
14 hydrothermal decomposition apparatus
15 hot compressed water
16 discharged hot water
17 biomass solid residue
18 enzyme
19-1 first enzymatic hydrolysis device
19-2 second enzymatic hydrolysis device
20-1 first sugar solution (hexose)
20-2 second sugar solution (pentose)
21 fermenter
22 alcohol fermentation liquid
23 ethanol
24 residue
25 refiner

BEST MODE(S) FOR CARRYING OUT THE INVENTION

Exemplary embodiments of the present invention are described with reference to the accompanying drawings. The present invention is not limited to the embodiments. Constituting elements in the embodiments include elements easily achieved by a person skilled in the art, or elements being substantially equivalent to those elements.

First Embodiment

A system of producing an organic material, i.e., alcohol, with use of biomass material according to an embodiment of the present invention is described with reference to the drawings. FIG. 1 is a schematic of an organic material production system using biomass material according to the embodiment. As shown in FIG. 1, an alcohol production system 10-1 using biomass material according to the present embodiment includes: a pretreatment device 12 that, for example, pulverizes the biomass material 11; a hydrothermal decomposition apparatus 14 that hydrothermally decomposes pretreated biomass material (e.g., straw in the present embodiment), i.e., a pulverized biomass 13, by causing it to countercurrently contact the hot compressed water 15, elutes lignin components and hemicellulose components into the hot compressed water 15, and separates the lignin components and the hemicellulose components from a biomass solid residue; a first enzymatic hydrolysis device 19-1 that treats cellulose in a biomass solid residue 17, discharged from the hydrothermal decomposition apparatus 14, with an enzyme (cellulase) 18 to enzymatically hydrolyze it to a sugar solution containing hexose; a first alcohol fermenter 21-1 that produces an alcohol (ethanol in the present embodiment) by fermentation using a first sugar solution (hexose solution) 20-1 obtained by the first enzymatic hydrolysis device 19-1; and a first refiner 25-1 that refines a first alcohol fermentation liquid 22-1, so as to separate it into a target product, i.e., ethanol 23, and a residue 24. From the hydrothermal decomposition apparatus 14, the hot compressed water, into which the lignin components and the hemicellulose components are eluted, is discharged as discharged hot water 16.

Biomass to be fed to the hydrothermal decomposition apparatus 14 is not limited to any specific type, and is a living organism integrated in material circulation in global biosphere or accumulation of organic materials derived from living organisms (see JIS K 3600 1258). In the present invention, particularly, cellulose resources of wood materials such as broadleaf trees and plant materials; agricultural wastes; and food wastes are preferably used.

The biomass material 11 is preferably broken into particles having a diameter of equal to or less than 5 millimeters, though not limited to this particle diameter. The present embodiment describes the pretreatment device 12 as an example of pulverizing equipment. The present invention is not limited to this example, and for example, cleaning equipment may be used as the pretreatment device 12. When the biomass material 11 is chaff for example, the biomass material 11 can be fed to the hydrothermal decomposition apparatus 14, without being subjected to pulverization with pulverizing equipment.

In the hydrothermal decomposition apparatus 14, the reaction temperature ranges from 180° C. to 240° C. preferably, and from 200° C. to 230° C. more preferably. This is because, at temperatures below 180° C., the hydrothermal decomposition takes place at a low rate and requires a longer time, increasing the apparatus size, which are not preferable. On the contrary, at temperatures above 240° C., the decomposition rate is too high and more cellulose components are transferred from the solid to the liquid, facilitating excessive decomposition of hemicellulose sugars, which are not preferable. Dissolution of cellulose components starts at about 140° C., dissolution of cellulose starts at about 230° C., and dissolution of lignin components starts at about 140° C. The temperature is preferably set within a range from 180° C. to 240° C. that allows cellulose to be remained in the solid, and that enables hemicellulose components and lignin components to be decomposed at adequate rates.

The reaction pressure is preferably set to a pressure higher by 0.1 MPa to 0.5 MPa than the saturated steam pressure of water at each temperature, which allows the hot compressed water to stay inside the body. The reaction time is preferably three minutes to ten minutes, not more than 20 minutes. This is because a longer reaction time increases the ratio of excessively decomposed products and is not preferable.

According to the present invention, for the flowage of the hot compressed water 15 and the flowage of the pulverized biomass 13 inside the device main body of the hydrothermal decomposition apparatus 14, the hot compressed water 15 and the pulverized biomass 13 are countercurrently contacted, preferably with stirred and flowed.

In the hydrothermal decomposition apparatus 14, the pulverized biomass 13 is fed from the left side in the figure, while the hot compressed water 15 is fed from the right side in the figure. Because the pulverized biomass 13 and the hot compressed water 15 move in an opposite direction to one another, the hot compressed water 15 (hot water, the liquid dissolving decomposed products) is moved while being soaked in solid particles by the counter-current flow against the solid, the biomass material 11.

When countercurrently contacting each other, the solid biomass material 11 is decomposed with the hot compressed water 15, and the resulting decomposed products are dissolved and transferred to the hot compressed water 15.

As a ratio of the solid to the liquid, the liquid ratio is preferably less, because it enables reduction in amount of water to be recovered and in amount of steam used for warming during the hydrothermal decomposition. The weight ratio of the biomass material and the hot compressed water both to be fed is, for example, 1:1 to 1:10 preferably, and 1:1 to 1:5 more preferably, though it varies accordingly depending on the apparatus configuration.

According to the present invention, in the hydrothermal decomposition apparatus 14, use of the counter-current flow transfers lignin components and hemicellulose components to the liquid, i.e., the hot compressed water 15, while allowing cellulose to remain in the solid, i.e., the biomass solid residue 14. In this way, the first sugar solution (hexose) 20 is obtained at the 1 first enzymatic hydrolysis device 19-1. Accordingly, it is possible to establish a fermentation process suitable for a hexose (fermentation suitable for an end product: in the present embodiment, the ethanol 23 is obtained by fermentation using the first alcohol fermenter 21-1, and refined to the first alcohol fermentation liquid 22-1).

According to the present invention, with use of a hydrothermal decomposition apparatus that causes counter-current contact, side reaction products (lignin components and hemicellulose components) resulting from the reaction for producing a target component, i.e., cellulose, (that is enzymatically saccharified to a hexose solution) are transferred into the hot compressed water. In this way, the cellulose-based biomass solid residue can be obtained. Accordingly, by efficiently saccharifying the cellulose and using the sugar solution as a base material, various types of organic materials (e.g., alcohols) can be produced efficiently.

By causing counter-current contact, their components are sequentially discharged in order of solubility in the hot compressed water. Further, due to the temperature gradient from where the biomass is fed to where the hot water is fed, excessive decomposition of hemicellulose components is prevented. As a result, pentose components can be recovered efficiently. Further, by causing the biomass material and the hot compressed water to countercurrently contact with each other, the heat is recovered, which is preferable in view of system efficiency.

Although the present embodiment describes an example that an alcohol, ethanol, is obtained by fermentation, the present invention is not limited to this example. Other than alcohols, substitutes for petroleum used as chemical product material, or amino acids used as food and feed materials can be obtained with a fermenter.

Examples of industrial products produced from a sugar solution as a base material may include liquefied petroleum gas (LPG), auto fuel, aircraft jet fuel, heating oil, diesel oil, various types of heavy oils, fuel gas, naphtha, and naphtha decomposed products such as ethylene glycol, ethanolamine, alcohol ethoxylate, vinyl chloride polymer, alkylaluminum, polyvinyl acetate (PVA), vinyl acetate emulsion, polystyrene, polyethylene, polypropylene, polycarbonate, methyl methacrylate (MMA) resin, nylon, and polyester. Thus, substitutes for industrial products derived from crude oil, which is fossil fuel, and sugar solution derived from biomass, which is a material for producing such substitutes, can be used efficiently.

Second Embodiment

Figure 2:
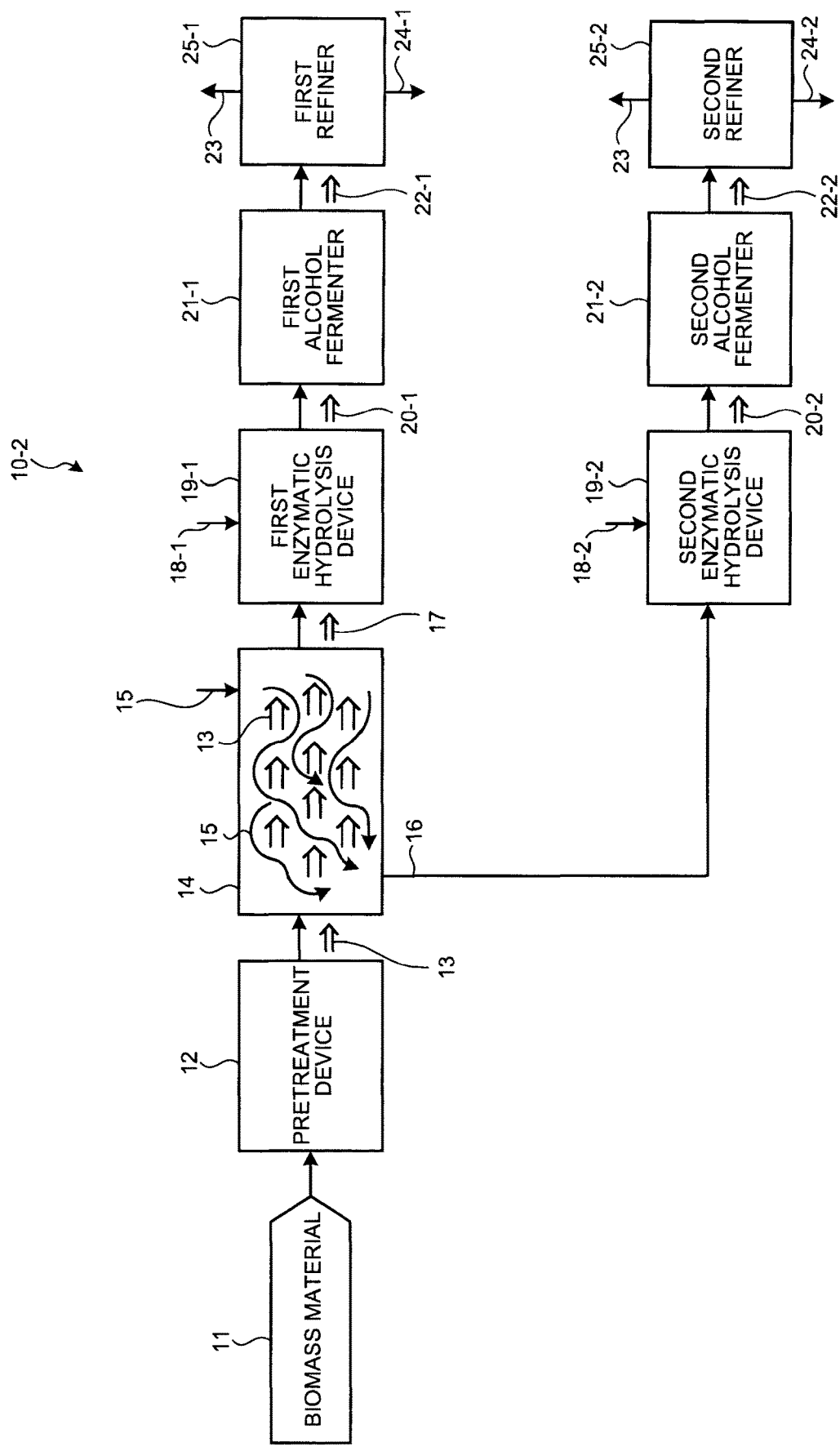
FIG. 2 is a schematic of an alcohol production system according to a second embodiment.

With reference to the drawings, the following describes a system of producing an organic material, i.e., alcohol, with use of biomass material according to an embodiment of the present invention. FIG. 2 is a schematic of an organic material production system using biomass material according to the present embodiment. As shown in FIG. 2, an alcohol production system 10-2 using biomass material according to the present embodiment is constituted by the system 10-1 shown in FIG. 1 that includes a second enzymatic hydrolysis device 19-2. The second enzymatic hydrolysis device 19-2 treats hemicellulose components, eluted into the discharged hot water 16 discharged from the hydrothermal decomposition apparatus 14, with an enzyme to enzymatically hydrolyze it to a second sugar solution 20-2 containing pentose. Two enzymatic hydrolysis devices, two alcohol fermenters, and two refiners are provided (the first enzymatic hydrolysis device 19-1, the second enzymatic hydrolysis device 19-2, the first alcohol fermenter 21-1, a second alcohol fermenter 21-2, the first refiner 25-1, and a second refiner 25-2). The ethanol 23 is obtained by performing an enzymatic hydrolysis process, an alcohol fermentation process, and an alcohol refining process that are suitable for each of the first sugar solution (hexose) 20-1 and the second sugar solution (pentose) 20-2.

In the present embodiment, the ethanol 23 can be produced by fermentation, using the second sugar solution (pentose) 20-2 obtained by the second enzymatic hydrolysis device 19-2.

The discharged hot water is not necessarily treated in a separate system. For example, a process subsequent to that performed at the enzymatic hydrolysis device, a process subsequent to that performed at the alcohol fermenter, or a process subsequent to that performed at the refiner may be arranged as common process, or other modification may be made appropriately.

According to the present invention, in the hydrothermal decomposition apparatus 14, use of the counter-current flow allows cellulose to remain in the solid phase which is the biomass solid residue 17. Accordingly, the first sugar solution (hexose) 20-1 is obtained by the first enzymatic hydrolysis device 19-1 for performing enzymatic hydrolysis. Further, hemicellulose components dissolved in the liquid phase which is the hot compressed water 15, are separated as the discharged hot water 16, and the second sugar solution (pentose) 20-2 is obtained by the second enzymatic hydrolysis device 19-2 for performing another enzymatic hydrolysis. This enables the first sugar solution and the second sugar solution to be separated efficiently and saccharified in different processes. Accordingly, fermentation processes suitable for hexose and pentose (fermentation suitable for an end product: e.g., ethanol fermentation) can be established.

As such, in the hydrothermal decomposition apparatus 14, use of the counter-current flow transfers a side reaction product and a lignin component soluble hot compressed water, both acting as inhibitors during enzymatic saccharification reaction for obtaining hexose, to the hot compressed water 15. Accordingly, the cellulose-based biomass solid residue 17 is obtained, improving the yield of pentose in the subsequent saccharification reaction.

On the other hand, hemicellulose components contained in the separated discharged hot water 16 is saccharified later at the second enzymatic hydrolysis device 19-2, so that a sugar solution containing pentose can be obtained. Then, in the first and second alcohol fermenters 18, 34 by using yeasts etc. suitable for hexose and pentose, ethanol can be obtained by fermentation individually and efficiently.

As described above, the present invention provides: an organic material production system and a method using biomass material that can produce, by transferring cellulose-based components and hemicellulose components from the biomass material to the hot compressed water and separating them from each other, sugar solutions suitable for the cellulose-based components and the himicellulose components (hexose sugar solution and pentose sugar solution), and that can efficiently produce, using the sugar solutions as base materials, various types of organic materials (e.g., alcohols, substitutes for petroleum, or amino acids). However, a conventional technology causes a phenomenon that a side reaction product inhibits enzymatic saccharification and a sugar yield is reduced.

INDUSTRIAL APPLICABILITY

As described, the system and method according to the present invention can separate cellulose-based components from biomass material, so as to efficiently produce a sugar solution. Further, using the sugar solution as a base material, various types of organic materials (e.g., alcohols, substitutes for petroleum, or amino acids) can be efficiently produced.

The invention claimed is:
1. An organic material production method using biomass material, the organic material production method consisting of:
(i) a pretreatment step and subsequently (ii) a hydrothermal decomposition step, in said order,
in the pretreatment step the biomass material is broken into particles having a diameter of equal to or less than 5 millimeters;
the hydrothermal decomposition step comprises a process of
feeding the biomass material and hot compressed water in a hydrothermal decomposition apparatus, a weight ratio of the biomass material and the hot compressed water being 1:1 to 1:10,
causing the biomass material and the hot compressed water to countercurrently contact with each other,
hydrothermally decomposing the biomass material in the hydrothermal decomposition apparatus to transfer a lignin component and a hemicellulose component as inhibitors for enzymatic saccharification from the biomass material to the hot compressed water while suppressing decomposition of a cellulose component of the biomass material, so as to obtain a cellulose-based biomass solid residue, the hydrothermally decomposing of the biomass material comprises:
providing a temperature gradient in the hydrothermal decomposition apparatus in which a temperature increases in a direction from an input for the biomass material into the hydrothermal decomposition apparatus to an input for the hot compressed water into the hydrothermal decomposition apparatus, wherein temperatures in the temperature gradient fall within a range of from 180° C. to 240° C.;
a first enzymatic hydrolysis process of treating, with an enzyme, cellulose in the cellulose-based biomass solid residue discharged from the hydrothermal decomposition apparatus, so as to enzymatically hydrolyze the cellulose to a sugar solution containing hexose;
a first fermentation process of producing, using the sugar solution obtained by the first enzymatic hydrolysis process, any one of alcohols, substitutes for petroleum, or amino acids by fermentation;
a second enzymatic hydrolysis process of treating, with an enzyme, the hemicellulose component in discharged hot water, so as to hydrolyze the hemicellulose com- ponent to a pentose solution, the discharged hot water containing the lignin component and the hemicellulose component;

a second fermentation process of producing, using the pentose solution obtained by the second enzymatic hydrolysis process, any one of alcohols, substitutes for petroleum, or amino acids by fermentation;

a first residue separation process of separating a first residue from the any one of alcohols, substitutes for petroleum, or amino acids produced at the first fermentation process; and a second residue separation process of separating a second residue from the any one of alcohols, substitutes for petroleum, or amino acids produced at the second fermentation process, wherein the inhibitors for enzymatic saccharification have a property of inhibiting the first enzymatic treatment and the first fermentative treatment.

2. The organic material production method according to claim 1, wherein a solubility of the lignin component and the hemicellulose component in the hot compressed water changes in the direction of the temperature gradient.

* * * * *